(12) United States Patent
Fridman et al.

(10) Patent No.: US 9,504,834 B1
(45) Date of Patent: Nov. 29, 2016

(54) PACEMAKER THRESHOLD TESTING BASED ON PULSE OXIMETER OUTPUT CURVE

(71) Applicants: Vladimir Fridman, Brooklyn, NY (US); Cesare Saponieri, Garden City, NY (US)

(72) Inventors: Vladimir Fridman, Brooklyn, NY (US); Cesare Saponieri, Garden City, NY (US)

( * ) Notice: Subject to any disclaimer, the term of this patent is extended or adjusted under 35 U.S.C. 154(b) by 0 days.

(21) Appl. No.: 14/727,097

(22) Filed: Jun. 1, 2015

(51) Int. Cl.
*A61N 1/365* (2006.01)
*A61N 1/37* (2006.01)
*A61N 1/372* (2006.01)

(52) U.S. Cl.
CPC .......... *A61N 1/36585* (2013.01); *A61N 1/371* (2013.01); *A61N 1/37247* (2013.01)

(58) Field of Classification Search
None
See application file for complete search history.

(56) References Cited

U.S. PATENT DOCUMENTS

| | | | |
|---|---|---|---|
| 4,813,421 A | 3/1989 | Baudino et al. | |
| 4,903,701 A | 2/1990 | Moore et al. | |
| 4,919,136 A | 4/1990 | Alt | |
| 5,312,454 A | 5/1994 | Roline et al. | |
| 5,586,556 A | 12/1996 | Spivey et al. | |
| 5,682,902 A | 11/1997 | Herleikson | |
| 6,537,225 B1 | 3/2003 | Mills | |
| 6,647,289 B2 | 11/2003 | Prutchi | |
| 7,907,992 B2 | 3/2011 | Ricke | |
| 2011/0144711 A1* | 6/2011 | Bornzin | A61N 1/3627 607/18 |

OTHER PUBLICATIONS

H. Weston Moses, James C. Mullin, A practical guide to cardiac pacing, Jan. 1, 2007, pp. 43, 41, 47, 49, 50, 55, 56, Lippincott Williams & Wilkins, US.

* cited by examiner

*Primary Examiner* — Erica Lee
(74) *Attorney, Agent, or Firm* — Michael J. Feigin, Esq.; Feigin & Fridman

(57) ABSTRACT

Methods of threshold testing and setting a voltage on an artificial pacemaker based on the output of a plethymograph, such as an oximeter, are disclosed herein. This is accomplished by determining blood volume in a limb or area of the body, and its change over time. As voltage is decreased in the pacemaker, a change in blood volume of the limb being measured by the oximeter is determined. This change can be a change in how often the blood volume level rises to its peak level and/or the blood volume level no longer rises substantially. Such changes, or lack thereof, can be based on a backup heart rate or no heart rate at all. Once the threshold voltage is determined where the artificial pacemaker ceases to cause a heartbeat, the voltage of the pacemaker can be set accordingly.

18 Claims, 4 Drawing Sheets

PACEMAKER THRESHOLD TESTING BASED ON PULSE OXIMETER OUTPUT CURVE

FIELD OF THE DISCLOSED TECHNOLOGY

The disclosed technology relates generally to artificial cardiac pacemakers and, more specifically, to threshold testing thereof.

BACKGROUND OF THE DISCLOSED TECHNOLOGY

Artificial cardiac pacemakers are typically calibrated after implantation and then re-calibrated periodically, such as every six months. Typically, a threshold voltage is determined by which, at a certain minimum voltage, the heart muscle is stimulated to contract, and then the artificial pacemaker is set at a voltage of about twice the threshold voltage. On the one hand, it is important for the inserted pacemaker to cause the heart to beat with regularity. On the other hand, since the pacemaker is battery-powered, with a limited battery life, and an electrical stimulus is being provided to the heart, the voltage should not be too high. The threshold voltage is defined as the minimum voltage needed to cause the heart to beat.

To detect a heart beat and measure the heart rate, the present method used, such as with threshold testing of an artificial pacemaker, is to use an EKG machine (electrocardiogram). The drawbacks to EKG's are the inconvenience to the patient in undressing and the time needed for preparation and carrying out the measurements. For example, patients are usually instructed to remove their jewelry. Men are instructed to remove their shirts. Women are often stripped down to a bra. The patient then lies on a bed or table while electrodes are attached, sometimes after shaving the patient. The electrode must be soaked in alcohol to improve conductivity in many cases. The patient must lie still and breathe slowly or hold his/her breath. The electrodes feel cold and stick to the skin.

What is needed in the art is a way to conduct pacemaker threshold testing without the patient having to undress, and, in some cases, to be shaved, as well as having electrodes attached.

SUMMARY OF THE DISCLOSED TECHNOLOGY

Embodiments of the disclosed technology include methods of threshold testing (defined as, "determining a minimum voltage or other measure of output required to cause a cardiac muscle to contract causing a heart beat"). In one stop, an artificial pacemaker (defined as "device outputting an electrical signal to a heart") is made to beat at a regular rate. Blood volume at a location on a limb (defined as "a finger, toe, hand, foot, arm, or leg") is measured, using a plethysmograph. The plethysmograph, for purposes of this disclosure, is "an instrument for measuring changes in volume within an organ," such as by using volumetic measurements or change in light refraction. The plethysmograph may be an oximeter.

Based on use of the plethysmograph, a correspondence between the regular rate and the output of the plethysmograph is determined, such as determining a period between an amount when each of a maximum and minimum reading is determined by means of or use of the plethymograph. After (or before) the correspondence is determined, such as at a patient's resting heart rate, the artificial pacemaker is manipulated to lower its output voltage over time. As the output voltage is lowered, it is determined when a lower or substantially lower voltage bound or limit at which said correspondence is no longer applicable, is reached. That is, below a certain voltage, the heart will not beat at the same rate, and this will be detected based on measurements of the plethysmograph (or as part of the measurements with an oximeter). Based on same, adjustments are made to the artificial pacemaker, such as setting its output voltage to two times lower voltage bound or limit.

A highest volume of the limb can be approximately at a time of the artificial pacemaker beat, and a lowest volume at a time just before the artificial pacemaker beat. Between the highest and lowest volume, the blood oxygen levels can be kept substantially or fully constant. A condition at or below the lowest volume outputted by the plethysmograph can occur more often when said voltage is below the lower voltage bound or limit, this condition corresponding to a backup heart rate.

In order to detect the correspondence between volume and pacemaker function, a graphical output of blood volume level versus time can be used. On such an output, finding a magnitude or time difference change in the blood volume can be used to make the determination.

The lower voltage bound can further be determined based on the regular rate of the artificial pacemaker being higher than a periodic rate at which the blood volume reaches a maximum.

Expressed differently, a method of threshold testing an artificial pacemaker can include the following steps. One can measure blood oxygen levels and blood volume levels at a specific location of a patient with an oximeter, and view the output of the measuring on a visual output showing the blood volume level versus time, to determine, at least in part, a heart rate based on a rate of jump in increase of blood volume level, as shown on the output. Then, one lowers the output voltage of the artificial pacemaker and determines if a substantial change has occurred. These steps are, in turn, repeated until a substantial change in the heart rate occurs. Then, one sets a voltage output of the pacemaker based on a voltage at which the substantial change occurs.

The determination of the heart rate can further include a step of determining substantially a magnitude difference, and/or substantially a distance between high and low points of the blood volume level, as shown in the output as part of determining the heart rate. An oximeter can be attached externally to a person and, when carrying out the step of determining the magnitude difference and/or the distance between the high and the low points of the blood volume level, a regular correspondence between heart rate and blood volume level can be further determined, using the oximeter.

In another way of describing methods of the disclosed technology, an artificial pacemaker is set to an output voltage, then blood oxygen and blood volume levels are measured with an external pulse oximeter while applying the output voltage (at periodic times). Based on output of the pulse oximeter, a blood volume level variation over time representative of a regular pulse is determined. At subsequently lower output voltages of the artificial pacemaker, the above is repeated to determine that the blood volume level variation over a period of time is below the level representative of a regular pulse. A new output voltage of the artificial pacemaker based on a threshold voltage determined is then set.

"Substantially" and "substantially shown," for purposes of this specification, are defined as "at least 90%," or as otherwise indicated. "Approximately" is defined as "within 15% of the time frame between each repeated period." Any device may "comprise" or "consist of" the devices mentioned there-in, as limited by the claims.

It should be understood that the use of "and/or" is defined inclusively such that the term "a and/or b" should be read to include the sets: "a and b," "a or b," "a," "b."

DETAILED DESCRIPTION OF EMBODIMENTS OF THE DISCLOSED TECHNOLOGY

Embodiments of the disclosed technology include methods of threshold testing and setting a voltage on an artificial pacemaker based on the output of a plethymograph, such as an oximeter. This is accomplished by determining blood volume in a limb or area of the body, and its change over time. As voltage is decreased in the pacemaker, a change in blood volume of the limb being measured by the oximeter is determined. This change can be a change in how often the blood volume level rises to its peak level and/or the blood volume level no longer rising substantially. Such changes, or lack thereof, can be based on a backup heart rate or no heart rate at all. Once the threshold voltage is determined where the artificial pacemaker ceases to cause a heartbeat, the voltage of the pacemaker can be set accordingly, usually at a voltage above the threshold voltage needed to cause the heart to beat.

Embodiments of the disclosed technology will become clearer in view of the following discussion of the figures.

Figure 1:
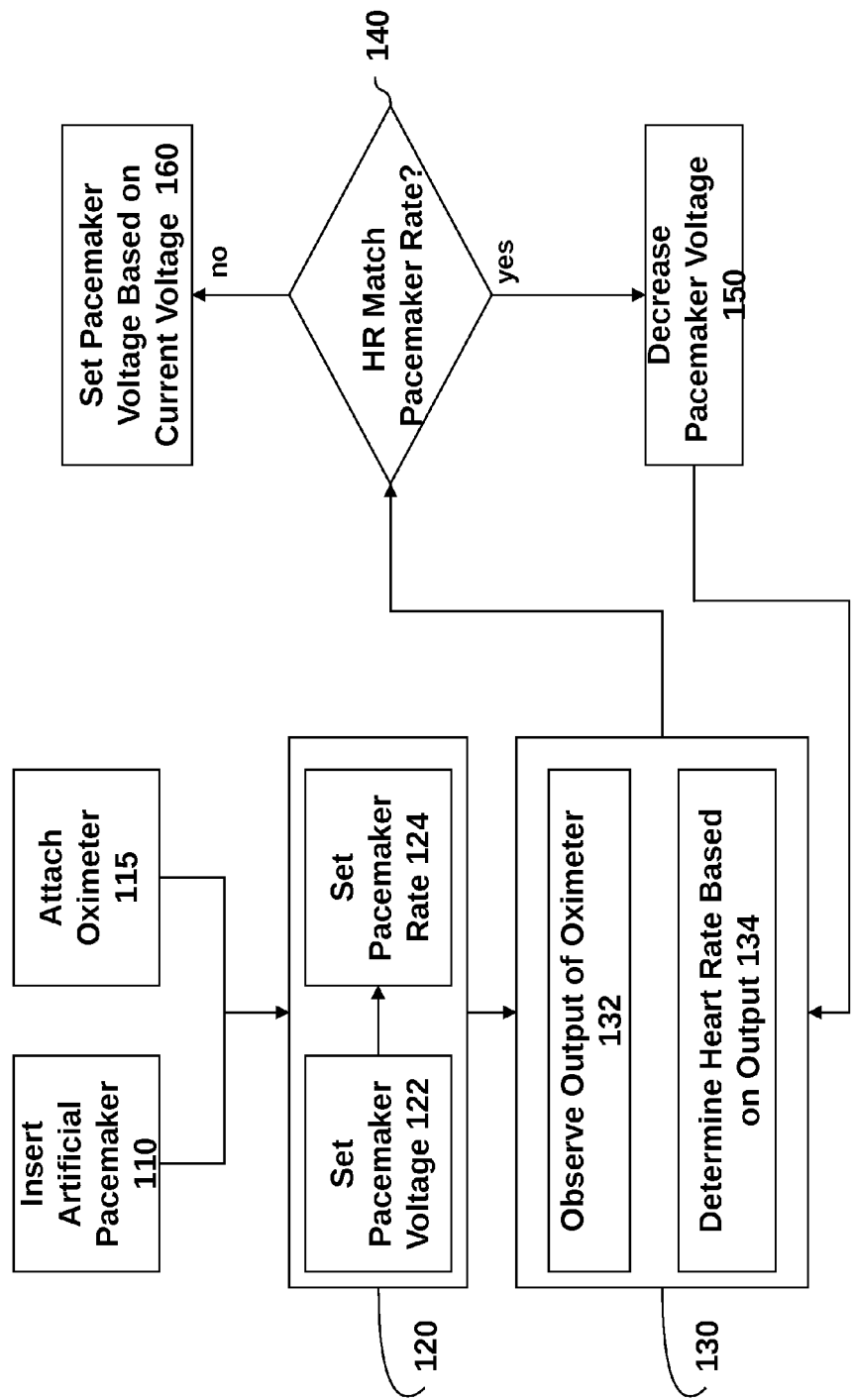
FIG. 1 shows a high level block diagram of steps to carry out embodiments of the disclosed technology.

FIG. 1 shows a high level block diagram of steps to carry out embodiments of the disclosed technology. In step 110 an artificial pacemaker is inserted. This involves a surgical process whereby an artificial pacemaker is inserted. For purposes of this disclosure, an artificial pacemaker is a battery-powered or other powered device with at least a timer and electrical output whereby, based on a timed interval or lack of a natural heart beat, electrodes or other electrical leads stimulate the cardiac muscle to contract. Further, an oximeter is attached in step 115. Unlike the artificial pacemaker, the oximeter is attached external to the patient/subject, such as to a finger, toe, arm, leg, or other appendage of the body. Instead of an oximeter, any plethymograph device can be used which measures blood volume. The oximeter/plethymograph device is used to detect a pulse of the cardiac cycle due to variation in blood volume in the skin caused by the pressure pulse of the cardiac cycle. The largest blood volume is ascertained approximately after the pulse and proportional thereto. In this manner, the systole and diastole pressure are viewable on proportional graphical output, similar to that of a direct EKG (electrocardiogram) monitor. As such, the oximeter can be used to replace the EKG, with the benefits resulting from using the oximeter, an externally attached device.

Referring back to FIG. 1, box 120 shows the initial settings of the pacemaker. The pacemaker is set with an initial voltage in step 122, as well as an initial rate in step 124. In threshold testing, the lower threshold is being determined because it is desirable as well as medically accepted practice, to find the lowest voltage needed to cause a cardiac muscle contraction with an artificial pacemaker. So, for example, in steps 122/124, the artificial pacemaker will be set with an initial output voltage of 3 volts and an initial rate of 100 BPM (beats per minute).

Box 130 of FIG. 1 shows the repetitive steps taken during the threshold testing. In a first iteration, the output of the oximeter (or other plethymograph) is observed in step 132. At this first iteration, in step 134, it is determined that the heart rate is equal to the pacemaker rate (set in step 124). Thus, decision block 140 must first be answered in the positive—that the heart rate matches the pacemaker rate. Then, a repeating series of steps is carried out, whereby the pacemaker voltage is decreased in step 150, and the steps in block 130 are carried out again. This cycle of determining the heart rate (box 130), determining that the heart rate is remaining steady at the initially observed rate (decision block 140), and decreasing the pacemaker voltage (step 150) is repeated until the heart rate decreases. The heart rate decrease is detected by receiving the output of the oximeter, indicating that the blood volume in the measured limb is no longer increasing (corresponding to no heart beat), or is increasing less often than the pacemaker rate (due to the patient's own backup rate from a natural heart beat or the cardiac muscle contracting only some of the time during which the present voltage is applied). At this point, the threshold voltage has been reached. The "threshold voltage" is defined as the voltage at which the blood volume levels measured with the plethymograph fail to increase to substantially a maximum blood volume at the same rate as the artificial pacemaker rate of electrical output.

Figure 2:
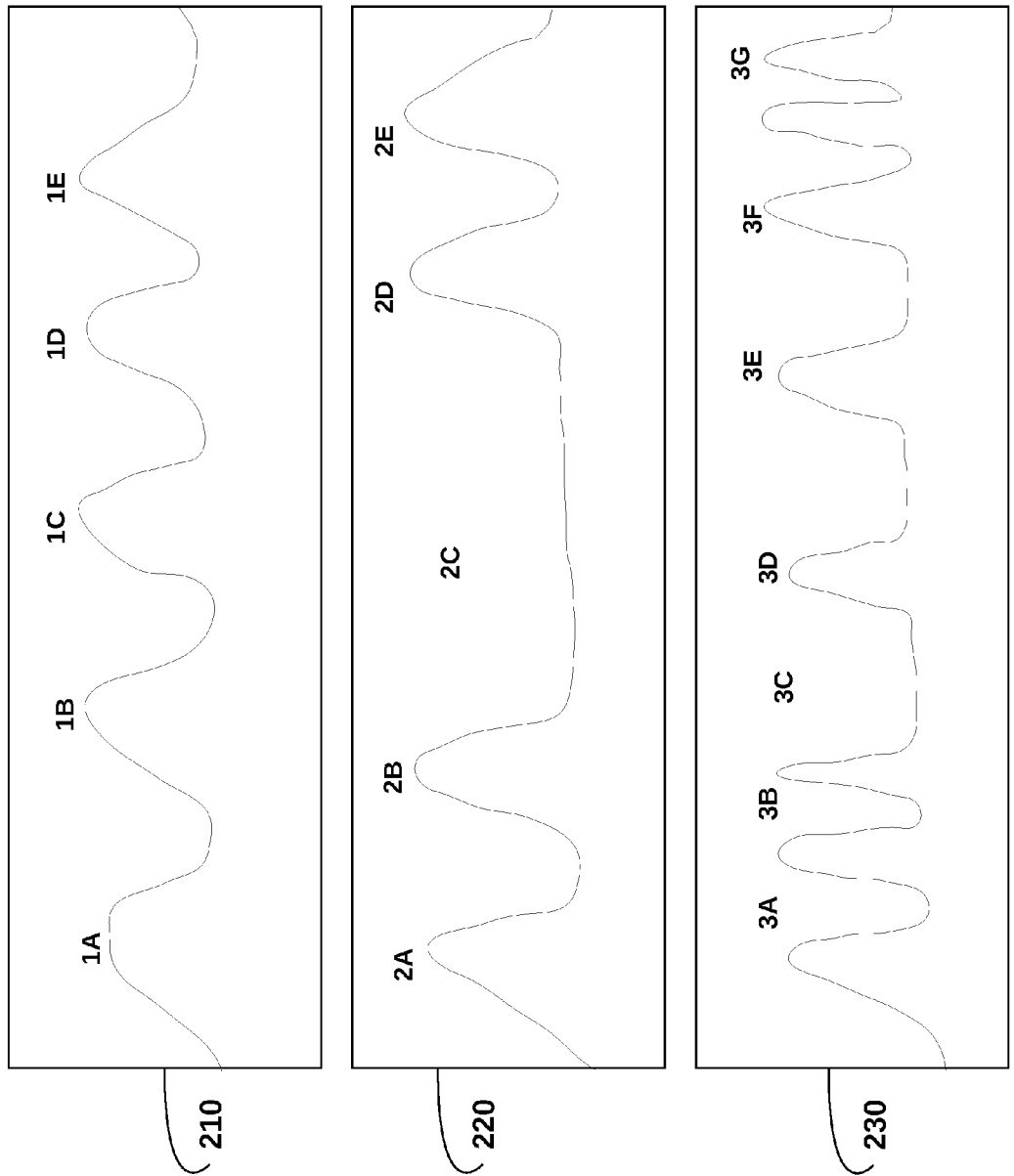
FIG. 2 shows graphical outputs of a plethymograph in conjunction with embodiments of the disclosed technology.

FIG. 2 shows graphical outputs of a plethymograph in conjunction with embodiments of the disclosed technology. The graphs 210, 220, and 230 include a visual graphical output of blood volume in a limb (Y-axis) versus time (X-axis). Graph 210 represents a regular heart beat. There is a regular, substantially equal, maximum blood volume (systole) determined by the oximeter or other plethymograph, as represented by the positions 1A through 1E. This indicates regular pacemaker function with a full cardiac muscle contraction. Such regular function, as shown in graph 210, can be indicative of a healthy normal heart, a properly functioning artificial pacemaker, and/or an artificial pacemaker above a threshold required to cause the heart to beat at each electrical impulse.

Graph 220 represents a sample of output when the voltage output from the artificial pacemaker drops below a minimum or bottom threshold for a proper cardiac muscle contraction. For example, at 2A, the pacemaker might be set and does output 3 volts. At 2B, this drops to 2 volts, and there is still no problem. Then, at 2C, the output drops to 1 volt, and the patient's blood volume fails to increase, indicating that the minimum threshold has been reached and/or crossed. Then, the pacemaker output is increased again, gradually (less than to the last voltage which caused a regular heart beat (at 2B)) or back to the last voltage where the heart beat properly. This is reflected at 2D and 2E.

Graph 230 shows a sample of output when the backup heart rate is shown, representing that the artificial pacemaker is failing to output enough electricity for a proper heart beat. Alternatively, graph 230 can show when the voltage of the artificial pacemaker is still causing some contraction of the heart muscle, but less than a full contraction. Here, 3A and 3B represent subsequent regular heart beats with a functioning artificial pacemaker above the minimum threshold. At 3C, 3D, and 3E are heart beats having lower magnitudes, reflective of either an artificial pacemaker having a lower than necessary output to effectuate a full cardiac contraction, or the artificial pacemaker having no effect and the beat representative of a backup heart rate and/or beat (defined as a cardiac contraction resulting from an electrical impulse generated by a biological and naturally occurring pacemaker in the body). During threshold testing, once one sees a flat line (2C) or lower magnitude blood volume levels (3C, 3D, 3E) then it is determined that the lower threshold voltage has been reached.

Figure 3:
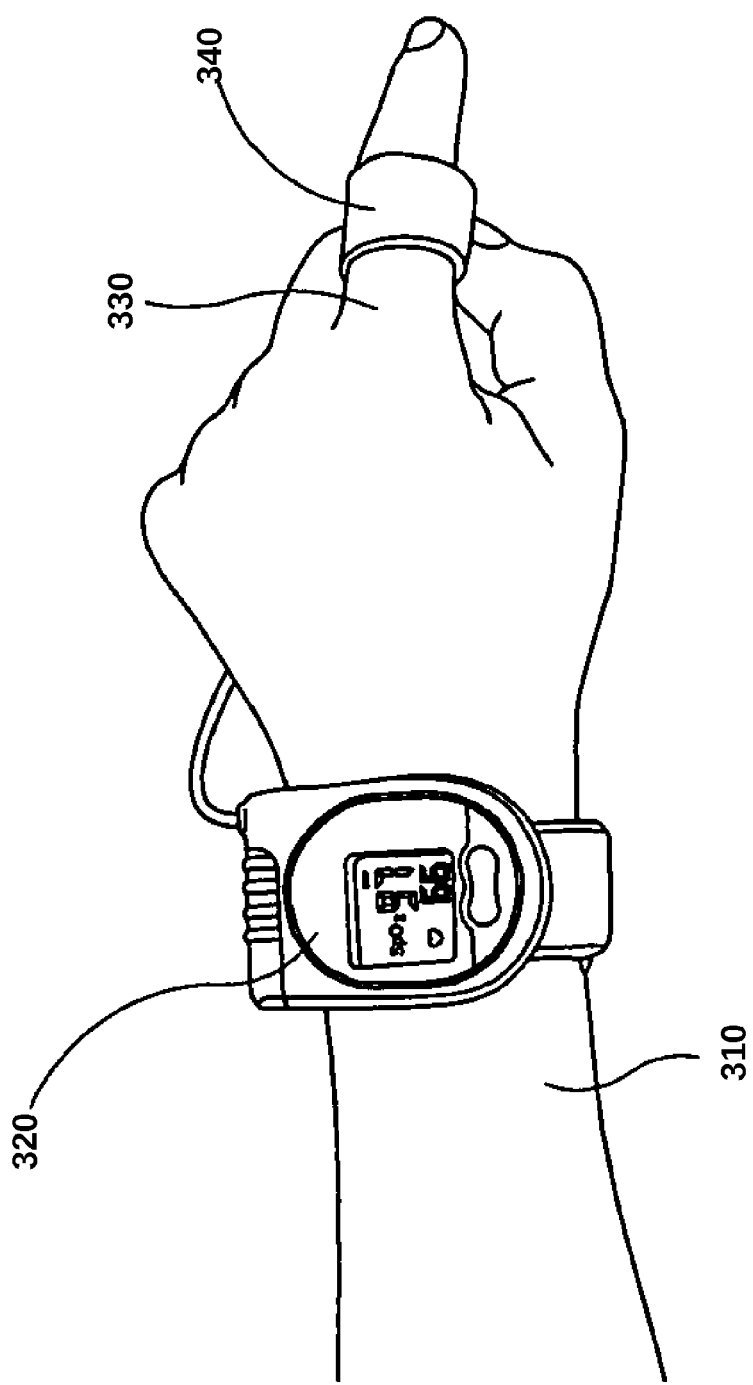
FIG. 3 shows an example of a pulse oximeter and/or plethymograph, which can be used to carry out embodiments of the disclosed technology.

FIG. 3 shows an example of a pulse oximeter and/or plethymograph which can be used to carry out embodiments of the disclosed technology. Here, the working end of the oximeter (or plethysmograph) 340 is wrapped around, or attached to, or on a limb. In this case the limb is a finger 330. The oximeter 340 uses light or other mechanisms to measure the blood volume in the limb 330 of the patient 310. This it outputted on a display 320. Such an output can show volume, heart rate determined by volume, and/or oxygen levels.

Figure 4:
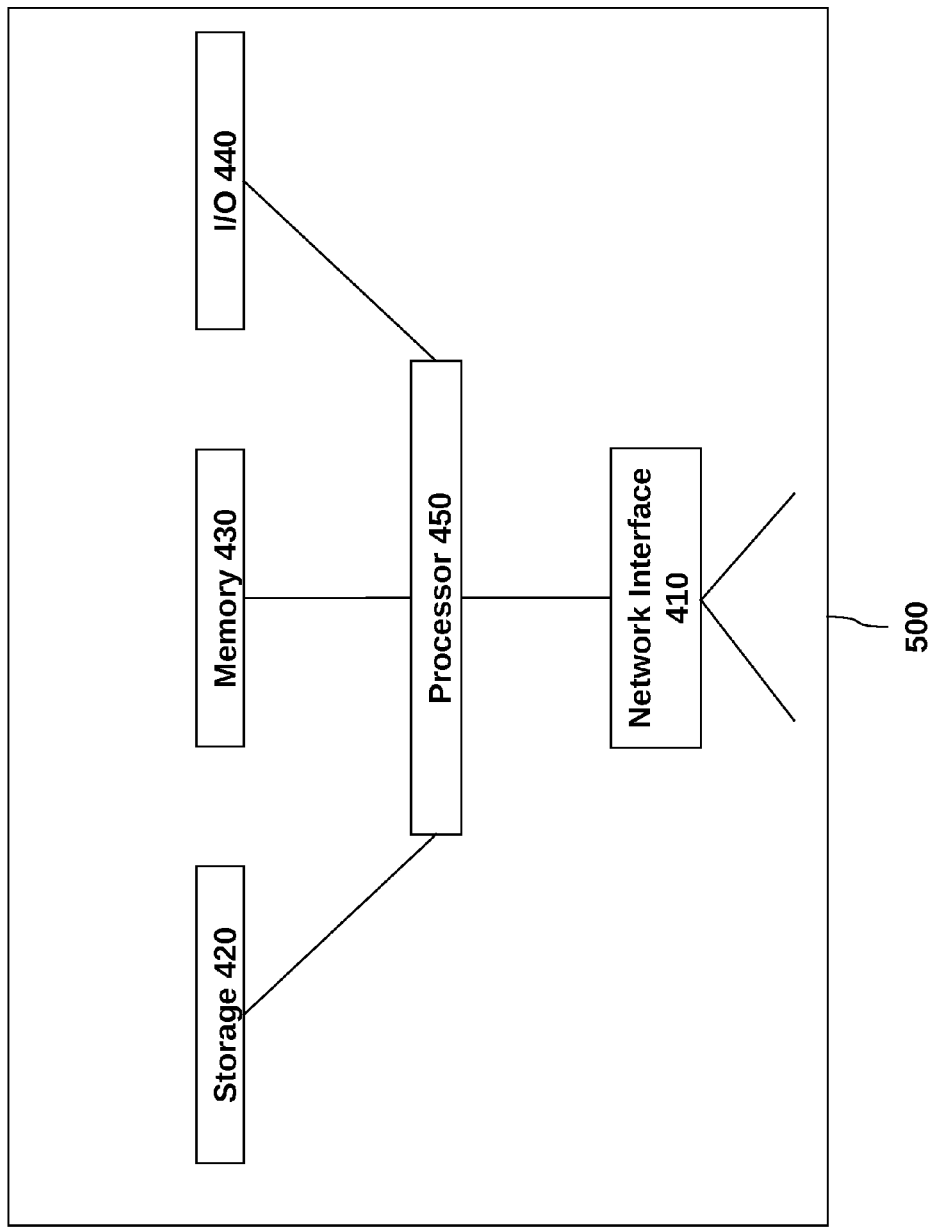
FIG. 4 shows a high-level block diagram of a device that may be used to carry out the disclosed technology.

FIG. 4 shows a high-level block diagram of a device that may be used to carry out the disclosed technology. Device 400 comprises a processor 450 that controls the overall operation of the computer by executing the device's program instructions which define such operation. The device's program instructions may be stored in a storage device 420 (e.g., magnetic disk, database) and loaded into memory 430 when execution of the console's program instructions is desired. Thus, the device's operation will be defined by the device's program instructions stored in memory 430 and/or storage 420, and the console will be controlled by processor 450 executing the console's program instructions. A device 400 also includes one or a plurality of input network interfaces for communicating with other devices via a network (e.g., the internet). The device 400 further includes an electrical input interface. A device 400 also includes one or more output network interfaces 410 for communicating with other devices. Device 400 also includes input/output 440 representing devices which allow for user interaction with a computer (e.g., display, keyboard, mouse, speakers, buttons, etc.). One skilled in the art will recognize that an implementation of an actual device will contain other components as well, and that FIG. 4 is a high level representation of some of the components of such a device for illustrative purposes. It should also be understood by one skilled in the art that the method and devices depicted in FIGS. 1 through 3 may be implemented on a device such as is shown in FIG. 4.

While the disclosed technology has been taught with specific reference to the above embodiments, a person having ordinary skill in the art will recognize that changes can be made in form and detail without departing from the spirit and the scope of the disclosed technology. The described embodiments are to be considered in all respects only as illustrative and not restrictive. All changes that come within the meaning and range of equivalency of the claims are to be embraced within their scope. Combinations of any of the methods and apparatuses described hereinabove are also contemplated and within the scope of the invention.

The invention claimed is:

1. A method of threshold testing an artificial pacemaker for calibration thereof, comprising steps of:
    setting an artificial pacemaker to beat at a regular rate;
    measuring blood volume at a location on a limb using a plethysmograph;
    detecting a correspondence between a cyclical increase and decrease of blood volume measured by said plethysmograph and said regular rate of said artificial pacemaker;
    setting said artificial pacemaker to output a voltage and decrease said voltage over time;
    determining substantially a lower voltage bound at which said correspondence is no longer applicable;
    adjusting said voltage of said artificial pacemaker as a result of said step of determining.

2. The method of claim 1, wherein output of said plethysmograph indicates a highest volume of said limb approximately at a time of said artificial pacemaker beat, and a lowest volume of said limb approximately at a time just before said artificial pacemaker beat.

3. The method of claim 2, wherein said plethysmorgraph is an oximeter measuring blood oxygen levels, and said blood oxygen levels remain substantially constant during said steps of measuring, setting, determining, and adjusting.

4. The method of claim 2, wherein a volume at or below said lowest volume is outputted by said plethysmograph more often when said voltage is below said lower voltage bound which corresponds to a backup heart rate.

5. The method of claim 2, wherein said adjusting comprises setting said artificial pacemaker to output a voltage of 2 times said lower voltage.

6. The method of claim 1, wherein said detecting of said correspondence is carried out by way of viewing output of said measuring on a graphical output of said blood volume level versus time.

7. The method of claim 6, wherein said correspondence is further determined by finding a magnitude or time difference change in said blood volume using said graphical output.

8. The method of claim 1, wherein said lower voltage bound is further determined based on said regulated rate of said artificial pacemaker being higher than a periodic rate at which said blood volume reaches a maximum.

9. A method of threshold testing an artificial pacemaker for calibration thereof, the method comprising steps of:
    measuring blood volume levels at a specific location of a patient with an oximeter;
    viewing output of said measuring on a visual output showing said blood volume level versus time;
    determining a cyclical blood volume level cycle;
    lowering output voltage of said artificial pacemaker;
    repeating said step of lowering and said step of determining until a substantial change in said blood volume level cycle occurs; and
    setting a voltage output of said pacemaker based on a voltage at which said substantial change occurred.

10. The method of claim 9, wherein said determination of said heart rate further comprising a step of determining substantially a magnitude difference and/or substantially a distance between high and low points of said blood volume level as shown in said output, as part of determining said heart rate.

11. The method of claim 10, further comprising determining if a substantial change in said magnitude difference and/or said distance between high and low points has occurred.

12. The method of claim 9, wherein said oximeter is attached externally to a person and, when carrying out said step of determining said magnitude difference, and/or said distance between said high and said low points of said blood volume level, a regular correspondence between heart rate and blood volume level is further determined.

13. The method of claim 9, wherein said substantial change is determined to occur at a lower voltage bound of proper functioning of said artificial pacemaker.

14. The method of claim 13, wherein said voltage output of said pacemaker is set at two times said voltage of said lower voltage bound.

15. A method of threshold testing an artificial pacemaker for calibration thereof, the method comprising:
    setting an artificial pacemaker to an output voltage;
    measuring blood volume level with an external pulse oximeter while applying said output voltage;
    determining, based on said measuring with said pulse oximeter, a blood volume level variation over time representative of a regular pulse;
    repeating said step of measuring at subsequently lower output voltages of said artificial pacemaker;
    determining, based on said output of said pulse oximeter, that a blood volume level variation over a period of time is below said blood volume level variation representative of said regular pulse;
    setting a new output voltage of said artificial pacemaker based on a threshold voltage and further based on said determining that said pulse rate is below a regular said pulse rate.

16. The method of claim 15, wherein said oximeter is further a plethysmograph, and said plethysmograph measures said blood volume level.

17. The method of claim 16, wherein said blood volume level variation is determined based on a greater distance in time between highest blood volume levels.

18. The method of claim 16, wherein said blood volume level variation is determined based on a blood volume level failing to rise after a period of time.

* * * * *